United States Patent [19]

Nagao

[11] Patent Number: 4,948,896
[45] Date of Patent: Aug. 14, 1990

[54] PROCESS FOR PREPARING PYRIDINE-2,3-DICARBOXYLIC ACID COMPOUNDS

[75] Inventor: Keishiro Nagao, Amagasaki, Japan

[73] Assignee: Daiso Co., Ltd., Osaka, Japan

[21] Appl. No.: 215,761

[22] Filed: Jul. 6, 1988

[30] Foreign Application Priority Data

Jul. 8, 1987 [JP] Japan .................. 62-171730

[51] Int. Cl.$^5$ .................. C07D 211/78; C07D 213/08
[52] U.S. Cl. .................. 546/250; 546/321
[58] Field of Search .................. 546/250, 321

[56] References Cited

U.S. PATENT DOCUMENTS

4,439,607  3/1984  Drabb .................. 546/89
4,460,776  7/1984  Wepplo .................. 546/250
4,723,011  2/1988  Doehner, Jr. .................. 546/250

FOREIGN PATENT DOCUMENTS

0067511  12/1982  European Pat. Off. .
3634975  4/1987  Fed. Rep. of Germany .
246369  12/1985  Japan .

OTHER PUBLICATIONS

Adrian Waldner, et al., "Pyridine-2,3-Dicarboxylic Acid Derivatives and New 1-Amino-1,4-Dihydropyridine-2,3-Dicarboxylic Acid Derivatives", Chemical Abstracts, 104: 207246w.

Johnson, Jerry Lee, "Quinolinic Acid Esters", Chemical Abstracts, 105: 208767z.

Stacey, Gilbert J., et al., "Pyridine Derivatives Inducing Tillering and Agricultural Compositions Containing Them", Chemical Abstracts, 98: 198023e.

Esmans, E. L., et al. "The Synthesis of 3-Acetyl-5-Alkylpyridines", Bull. Soc. Chim. Belg., vol. 82, no. 5-6, 1973, pp. 435-439.

March, J. *Advanced Organic Chemistry*, 3rd ed. (1985).

Primary Examiner—John M. Ford
Assistant Examiner—Robert C. Whittenbaugh
Attorney, Agent, or Firm—Wegner & Bretschneider

[57] ABSTRACT

Improved process for preparing pyridine-2,3-dicarboxylic acid compounds of the formula:

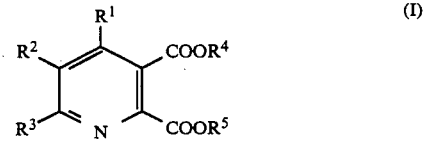

wherein $R^1$ and $R^3$ are each H, (un)substituted alkyl, or (un)substituted phenyl; $R^2$ is H, (un)substituted alkyl, (un)substituted phenyl, alkylthio, alkoxy, (un)substituted phenylthio, (un)substituted phenoxy, halogen, alkoxycarbonyl, aminocarbonyl which may optionally be substituted, or cyano; or both of $R^1$ and $R^2$ or both $R^2$ and $R^3$ may combined together to form a divalent alkylene; and $R^4$ and $R^5$ are each alkyl which are useful as an intermediate for preparing herbicidally effective compounds, which comprises reacting an enone (II) and an aminodiester (III) of the formulae:

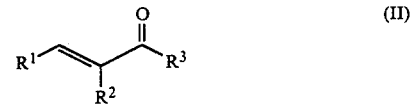

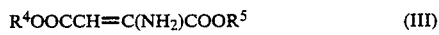

6 Claims, No Drawings

PROCESS FOR PREPARING PYRIDINE-2,3-DICARBOXYLIC ACID COMPOUNDS

This invention relates to a process for preparing pyridine-2,3-dicarboxylic acid compounds which are useful as an intermediate for preparing some compounds useful as herbicides. More particularly, it relates to an improved process for preparing pyridine-2,3-dicarboxylic acid compounds of the formula:

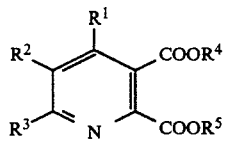
(I)

wherein $R^1$ and $R^3$ are the same or different and are each a hydrogen atom, a substituted or unsubstituted straight chain or branched chain alkyl having 1 to 4 carbon atoms, or a substituted or unsubstituted phenyl; $R^2$ is a hydrogen atom, a substituted or unsubstituted straight chain or branched chain alkyl having 1 to 4 carbon atoms, a substituted or unsubstituted phenyl, a straight chain or branched chain alkylthio having 1 to 4 carbon atoms, a straight chain or branched chain alkoxy having 1 to 4 carbon atoms, a substituted or unsubstituted phenylthio, a substituted or unsubstituted phenoxy, a halogen atom, a straight chain or branched chain alkoxycarbonyl having 1 to 4 carbon atoms in the alkoxy moiety, an aminocarbonyl which may optionally have a substituent, or cyano; or both of $R^1$ and $R^2$ or both $R^2$ and $R^3$ may combine together to form a divalent alkylene selected from trimethylene, tetramethylene and pentamethylene; and $R^4$ and $R^5$ are the same or different and are each a straight chain or branched chain alkyl having 1 to 4 carbon atoms.

PRIOR ART

It has been known that some pyridine-2,3-dicarboxylic acid compounds are useful as an intermediate for preparing compounds which are used as herbicides. For example, it is disclosed in U.S. Pat. No. 4,439,607 that pyridine-2,3-dicarboxylic acid compounds are useful as intermediates in the manufacturing of the herbicidally effective 2-(2-imidazolin-2-yl)pyridine compounds of the formula:

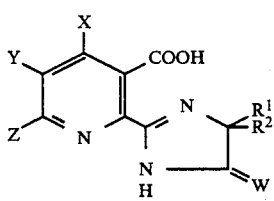

wherein $R^1$ is $C_1-C_4$ alkyl, $R^2$ is $C_1-C_4$ alkyl or $C_3-C_6$ cycloalkyl or $R^1$ and $R^2$ may form together $C_3-C_6$ cycloalkyl optionally substituted with methyl; W is O or S; X is hydrogen, halogen or methyl, with proviso that when Y and Z form together a ring and YZ is —($CH_2$-)$_n$—(n 3 or 4), then X is hydrogen; Y and Z are each hydrogen, halogen, $C_1-C_6$ alkyl, alkoxy, alkylthio, phenoxy, haloalkyl, nitro, cyano, alkylsulfonyl, substituted or unsubstituted phenyl, etc. Similar disclosures are included in many other literatures, for example, U.S. Pat. No. 4,460,776, European Patent Publication No. 0041623 (cf. Chemical Abstracts, 96, 199687q).

It is also known that the pyridine-2,3-dicarboxylic acid compounds can be prepared by various processes. For example, it is disclosed in U.S. Pat. No. 4,460,776 that 6-substituted-pyridine-2,3-dicarboxylic acids can be prepared by condensing 1-amino-1,2-ethylenedicarboxylic acid esters with acetylenic ketones as shown in the following reaction scheme:

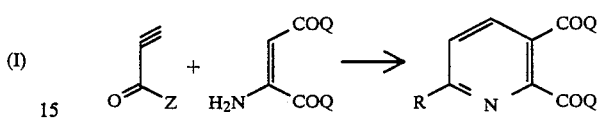

wherein Z is hydrogen, $C_1-C_6$ alkyl, or phenyl optionally substituted with $C_1-C_4$ alkyl, halogen, $C_1-C_4$ alkoxy, nitro or $C_1-C_4$ alkylthio and Q is $C_1-C_4$ alkoxy. According to this process, however, a large amount of acetylide, trimethylsilylacetylene etc. are required for preparing the starting acetylenic ketones, and hence, the process is costly.

It is disclosed in European Patent Publication No. 161,221 (=Japanese Patent First Publication (Kokai) No. 246369/1985, cf. Chemical Abstracts, 104, 207246w) that 4,5-disubstituted-pyridine-2,3-dicarboxylic acid compounds are prepared by condensing α-halomaleic imide compounds with α,β-unsaturated aldehyde N,N-dialkylhydrazone, followed by treating the reaction product with an acid or under heating as shown in the following reaction scheme:

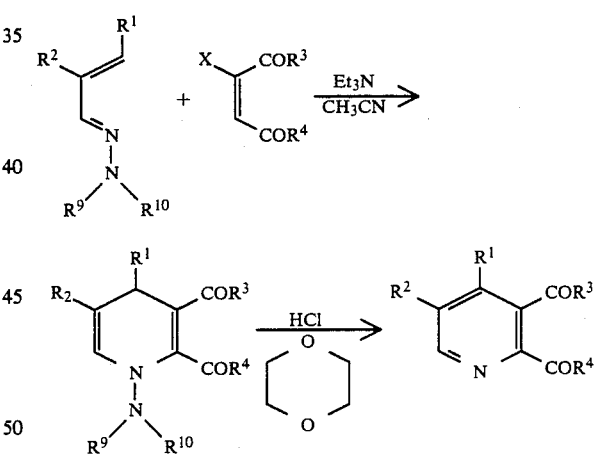

wherein $R^1$ is hydrogen, substituted or unsubstituted alkyl, alkylthio, alkoxy, phenyl or phenoxy, $R^2$ is the same as $R^1$, or halogen, $R^3$ and $R^4$ are each hydroxy, amino, mono- or disubstituted amino, alkoxy, etc., and $R^9$ and $R^{10}$ are each alkyl, cycloalkyl, aralkyl or aryl, or $R^9$ and $R^{10}$ are combined to form alkylene or oxaalkylene. However, this process is disadvantageous in that (1) the starting α-halomaleic imide compounds are prepared through several steps with low overall yield and (2) the process requires to use expensive asymmetric hydrazine which can not be recovered after the reaction.

It is disclosed in Brazilian Patent Publication No. 85/2364 (=U.S. Appln. No. 612,531, cf. Chemical Abstracts, 105, 208767z) that 5,6-disubstituted-pyridine-2,3-dicarboxylic acid esters are prepared by reacting enamines and alkoxymethylene oxalacetates with heating in the presence of ammonia as shown in the following reaction scheme:

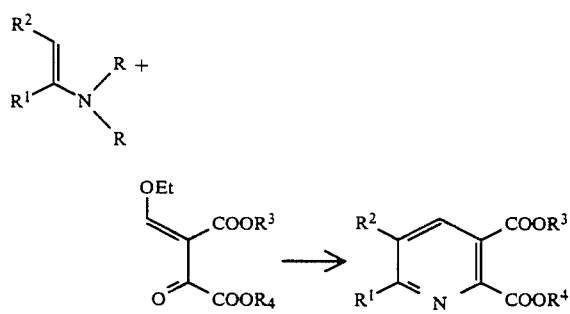

wherein R¹ and R² are each hydrogen, alkyl, phenyl, tolyl, or are combined to form a fused ring, and R³ and R⁴ are each hydrogen or alkyl. This process is, however, disadvantageous in that (1) the enamines must be prepared separately, and the enamines are prepared in comparatively lower yield in case of lower aliphatic aldehyde derivatives, (2) the amines used for preparing enamines must be separated and recovered after reaction, and (3) the reaction must be carried out in the presence of ammonia which requires careful attention during the reaction procedure.

It is also disclosed in U.S. Pat. No. 4,723,011 (=Japanese Patent First Publication (Kokai) No. 106081/1987, German Patent Offenlegungsschrift 3,634,975, cf. Chemical Abstracts, 107, 134206h) that 4,5,6-trisubstituted-pyridine-2,3-dicarboxylic acid compounds are prepared by reacting alkenylketones with halo-oxalacetic acid compounds in the presence of an ammonium salt as shown in the following reaction scheme:

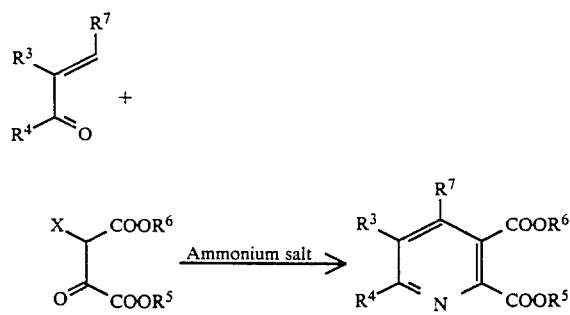

wherein $R^3$ is hydrogen, halogen, $C_1$–$C_6$ alkyl, alkenyl, phenyl, or substituted phenyl, $R^4$ and $R^7$ are each hydrogen, $C_1$–$C_6$ alkyl, alkenyl, phenyl, or substituted phenyl, $R^5$ and $R^6$ are each $C_1$–$C_4$ alkyl.

It is disclosed in European Patent Publication No. 67511 (cf. Chemical Abstracts, 98, 198028e) that 5-phenylpyridine-2,3-dicarboxylic acid compounds are prepared by reacting 1-amino-1,2-ethylenedicarboxylic acid esters with 1-phenyl-2-dimethylaminoacrolein as shown in the following reaction scheme:

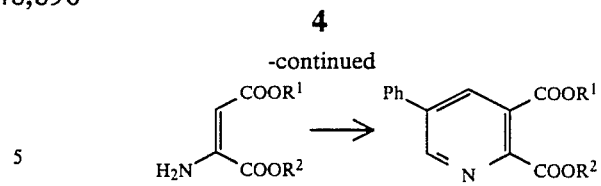

wherein $R^1$ and $R^2$ are each alkyl and Ph is phenyl or a substituted phenyl.

In the known processes as mentioned above, some removable groups (e.g. halogen, substituted amino, etc.) are contained in the starting materials in order to facilitate aromatization of the intermediate 1,4-dihydropyridines to pyridine nucleus, but introduction of these removable groups inevitably complicates the synthesis of the starting material and pushes cost higher.

Besides, it is known that pyridine nucleus can also be formed by reacting an acrolein derivative and 1-amino-1-buten-3-one as shown in the following reaction scheme [cf. E. L. Esmans, F. C. Alderweireldt, Bull. Soc. Chim. Belg., 82, 435 (1973)], while it has no direct relation with the process for preparing pyridine-2,3-dicarboxylic acid compounds,

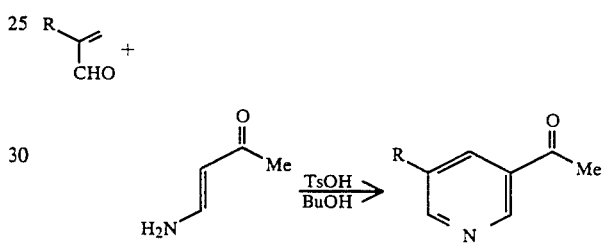

wherein R is methyl, ethyl, propyl, or isopropyl.

BRIEF DESCRIPTION OF THE INVENTION

The present inventor has intensively studied to eliminate the problems in the known processes as mentioned above and have found that the desired pyridine-2,3-dicarboxylic acid compounds can be prepared by reacting specific enones and aminodiesters in a single step and in high yield.

An object of the invention is to provide an improved process for preparing pyridine-2,3-dicarboxylic acid compounds useful as an intermediate for preparing herbicides. Another object of the invention is to provide a process for preparing said compounds in higher yield by using less expensive starting materials in a simple step. These and other objects and advantages of the invention will be apparent to those skilled in the art from the following description.

DETAILED DESCRIPTION OF THE INVENTION

According to this invention, the desired pyridine-2,3-dicarboxylic acid compounds of the formula (I) can be prepared by reacting enones of the formula (II) with aminodiesters of the formula (III).

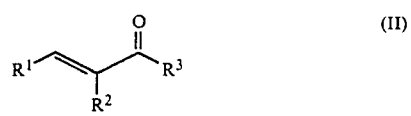

(II)

$$R^4OOCCH=C(NH_2)COOR^5 \qquad (III)$$

wherein $R^1$, $R^2$, $R^3$, $R^4$, and $R^5$ are as defined above.

The groups of $R^1$, $R^2$, $R^3$, $R^4$, and $R^5$ in the formulae (I), (II) and (III) of this invention denote more specifically the following groups.

$R^1$ and $R^3$ are the same or different and are each a hydrogen atom; an unsubstituted straight chain or branched chain alkyl having 1 to 4 carbon atoms, such as methyl, ethyl, n-propyl, isopropyl, n-butyl, isobutyl, sec-butyl, tert-butyl; a substituted alkyl having 1 to 4 carbon atoms, wherein the substituent is selected from one to three members of hydroxy, an alkoxy having 1 to 4 carbon atoms, an alkylthio having 1 to 4 carbon atoms, a halogen atom (e.g. fluorine, chlorine, bromine), phenyl, phenoxy, phenylthio (said phenyl, phenoxy and phenylthio having optionally a substituent the same as mentioned hereinafter), cyano, an alkoxycarbonyl having 1 to 4 carbon atoms in the alkoxy moiety, and an aminocarbonyl being optionally substituted by one or two alkyls having 1 to 4 carbon atoms, for example, 3-hydroxybutyl, methoxymethyl, 4-methylthiopropyl, 3-chloropropyl, 4-bromobutyl, trifluoromethyl, benzyl, pchlorobenzyl, phenoxymethyl, 3-phenylthiopropyl, 2-cyanoethyl, 3-butoxycarbonylpropyl, 2-(N,N-dimethylaminocarbonyl)ethyl, etc.; phenyl; a phenyl substituted by a member selected from the group consisting of hydroxy, a halogen atom, an alkoxy having 1 to 4 carbon atoms, an alkylthio having 1 to 4 carbon atoms, an amino being optionally substituted by one or two alkyls having 1 to 4 carbon atoms, an alkanoylamino or alkanoyloxy having 1 to 4 carbon atoms in the alkanoyl moiety, an alkoxycarbonyl having 1 to 4 carbon atoms in the alkoxy moiety, an aminoalkanoyl being optionally substituted by one or two alkyls having 1 to 4 carbon atoms, cyano, nitro, and nitroso, for example, p-hydroxyphenyl, p-butoxyphenyl, p-chlorophenyl, o-methylthiophenyl, p-dimethylaminophenyl, pacetamidophenyl, m-isobutyryloxyphenyl, m-ethoxycarbonylphenyl, N,N-dimethylaminocarbonylphenyl, m-cyanophenyl, onitrophenyl, p-nitrosophenyl, etc.

$R^2$ includes the same groups as $R^1$ as mentioned above, and further includes a straight chain or branched chain alkylthio having 1 to 4 carbon atoms, a straight chain or branched chain alkoxy having 1 to 4 carbon atoms, a substituted or unsubstituted phenylthio, a substituted or unsubstituted phenoxy, a halogen atom (e.g. fluorine, chlorine, bromine), a straight chain or branched chain alkoxycarbonyl having 1 to 4 carbon atoms in the alkoxy moiety, an aminocarbonyl which may optionally have a substituent, or cyano, wherein the alkyl and phenyl are the same as mentioned above as to $R^1$ and $R^3$, and the alkylthio and alkoxy include, for example, methylthio, methoxy, tertbutoxy, etc.

In the substituted phenylthio and phenoxy, the substituents on the phenyl ring are the same as the substituents for phenyl in $R^1$ and $R^3$ as mentioned herein above. The substituted phenylthio and phenoxy include, for example, p-hydroxyphenylthio, p-methoxyphenoxy, p-chlorophenoxy, o-methythiophenoxy, p-dimethylaminophenoxy, pacetamidophenylthio, p-butyryloxyphenoxy, p-ethoxycarbonylphenoxy, N,N-dimethylaminocarbonylphenoxy, o-cyanophenoxy, o-nitrophenoxy, p-nitrosophenoxy, etc. Suitable examples of alkoxycarbonyl are methoxycarbonyl, isobutyloxycarbonyl, etc. and suitable examples of aminocarbonyl are N-methyl-N-benzylaminocarbonyl, etc.

Both of $R^1$ and $R^2$ or both $R^2$ and $R^3$ may combine together to form a divalent alkylene, such as trimethylene, tetramethylene and pentamethylene.

$R^4$ and $R^5$ are the same or different and are each a straight chain or branched chain alkyl having 1 to 4 carbon atoms, such as methyl, ethyl, n-propyl, isopropyl, n-butyl, isobutyl, sec-butyl, and tert-butyl.

The process of this invention is shown by the following reaction scheme [A]:

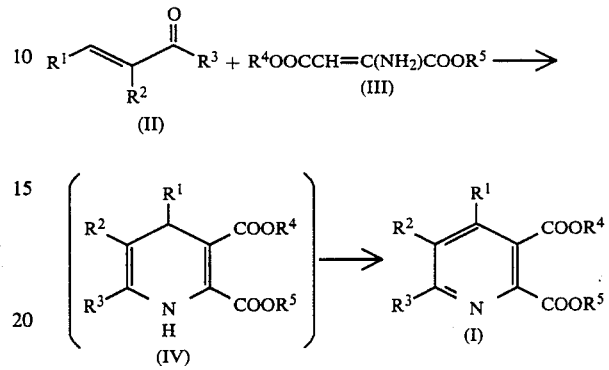

wherein $R^1$, $R^2$, $R^3$, $R^4$, and $R^5$ are as defined above.

The process of this invention is characteristic in that the enones of the formula (II) can easily be condensed with the aminodiesters of the formula (III) and that the resulting 1,4-dihydropyridines of the formula (IV) loses easily hydrogen atom under the reaction conditions to give the desired pyridine-2,3-dicarboxylic acid compounds of the formula (I) in a single step and in high yield.

The starting enones (II) and aminodiesters (III) used in this invention can easily be prepared from cheap and readily available compounds by a known process.

Examples of the enones (II) are acrolein, methacrolein, crotonaldehyde, methyl vinyl ketone, α-ethylacrolein, α-n-butylacrolein, 4-methyl-2-hexenal, α-methoxymethlacrolein α-trifluoromethylacrolein, α-(p-methoxybenzyl)acrolein, α-(p-chlorophenyl)acrolein, cinnamaldehyde, 2-propenyl phenyl ketone, p-chlorophenyl vinyl ketone, α-chloro-β-phenylacrolein, α-ethoxyacrolein, α-phenylethylthioacrolein, methyl α-formylacrylate, α-(2-cyanoethyl)acrolein, α-(p-acetamidophenyl)acrolein, β-(o-nitrophenyl)acrolein, α-methylenecyclopentanone, 1-formylcyclopentene, etc.

Examples of the aminodiesters (III) are dimethyl 1-amino-1,2-ethylenedicarboxylate, diethyl 1-amino-1,2-ethylenedicarboxylate, dibutyl 1-amino-1,2-ethylenedicarboxylate, etc.

These enones (II) and aminodiesters (III) are usually used in an equimolar amount but a slightly excess amount of enones (II) may be used.

The process of this invention can be carried out by mixing the enones (II) and the aminodiesters (III) without using any solvent or in an appropriate organic solvent.

The organic solvent is preferably a neutral solvent in view of less side reaction and easier work-up of the reaction, but organic carboxylic acid solvents may also be used. However, amine solvents such as triethylamine are not suitable because these solvents interfer the dehydrogenation of 1,4-dihydropyridines (IV) and thereby induce undesirable side reactions.

Suitable examples of the neutral solvent are alcohols (e.g. methanol, ethanol, butanol, ethylene glycol, etc.), nitriles (e.g. acetonitrile, etc.), esters (e.g. ethyl acetate, methyl propionate, etc.), ethers (e.g. diethyl ether, tetrahydrofuran, dioxane, ethylene glycol dimethyl ether, etc.), halogenated hydrocarbons (e.g. methylene chloride, 1,2-dichloroethane, 1,1,1-trichloroethane, etc.), carboxylic acid amides (e.g. N,N-dimethylformamide, N-methylpyrrolidone, etc.), sulfoxides (e.g. dimethylsulfoxide, etc.), sulfones (e.g. tetramethylenesulfone, etc.), aromatic hydrocarbons (e.g. benzene, toluene, etc.), and the like. These solvents may be used alone or in combination of two or more thereof. Suitable examples of organic carboxylic acid solvent are acetic acid, propionic acid, etc. Among the organic solvents, particularly preferred ones are alcohols, carboxylic acid amides, sulfoxides and carboxylic acids which have high polarity.

The reaction of this invention may be carried out merely by heating the mixture of the starting enone (II) and aminodiester (III) in an appropriate organic solvent or without using any solvent as mentioned above, but in order to shorten the reaction time and to suppress the undesirable side reactions, it is preferable to add acid to the reaction system in a catalytic amount, e.g. 0.01 to 10 parts by weight to 100 parts by weight of the starting enones (II). The acid includes inorganic strong acids (e.g. hydrochloric acid, sulfuric acid, etc.), organic sulfonic acids (e.g. methanesulfonic acid, p-toluenesulfonic acid, etc.), organic carboxylic acids (e.g. acetic acid, etc.), among which organic sulfonic acids are particularly preferable.

When the reaction of this invention is carried out in the presence of the above acid catalyst, it is preferable to remove the moisture within the reaction system in order to prevent hydrolysis of the aminodiesters (III).

The reaction temperature may vary depending on the kinds of solvent and catalyst used therein, but is preferably in the range of 50° to 150° C. When the reaction is carried out at lower than 50° C, the intermediate 1,4-dihydropyridines (IV) is too slowly dehydrogenated. On the other hand, when the reaction is carried out at higher than 150° C., decomposition of pyridine-2,3-dicarboxylic acid compounds (I) is unfavorably observed.

When the reaction is carried out by using an organic solvent having a boiling point of 50° to 150° C., it is most preferable to carry out the reaction under reflux temperature unless the reaction is affected by raising the temperature to the boiling point of the solvent.

After the completion of the reaction, the desired pyridine-2,3-dicarboxylic acid compounds (I) can be isolated and purified from the reaction mixture by any conventional purification methods, such as extraction with solvent, distillation, recrystallization, chromatography, and the like to give a highly pure product which is useful as an intermediate for preparing herbicidally effective compounds.

According to this invention, the desired pyridine-2,3-dicarboxylic acid compounds can be prepared in high yield and high purity by one step reaction within a very short reaction time from cheap and easily available enones and aminodiesters, and hence, this invention is valuable for industrial production of the desired pyridine-2,3-dicarboxylic acid compounds.

This invention is illustrated by the following Examples but should not be construed to be limited thereto. In Examples, the degree of reaction is shown by the degree of consumption of aminodiesters (III) by gas chromatographic analysis, and the purity of the product is determined by gas or liquid chromatographic analysis.

EXAMPLE 1

Diethyl 1-amino-1,2-ethylenedicarboxylate (1.0 g) and acrolein monomer (0.39 g) are dissolved in n-butanol (10 ml), and thereto is added p-toluenesulfonic acid (20 mg). The mixture is refluxed for 10 hours, and thereto is added additional acrolein monomer (0.1 g), and the mixture is refluxed for 5 hours (the degree of reaction of aminodiester is 91%). After distilling off the solvent, the residue is distilled under reduced pressure to give diethyl pyridine-2,3-dicarboxylate (0.86 g, 72.3%). The product has a boiling point of 135°–145° C. (3 Torr) and a purity of 96.4% by gas chromatographic analysis.

EXAMPLE 2

Diethyl 1-amino-1,2-ethylenedicarboxylate (1.7 g) and α-ethylacrolein (0.84 g) are dissolved in n-butanol (10 ml), and thereto is added p-toluenesulfonic acid (35 mg). The mixture is refluxed for 15 hours (the degree of reaction of aminodiester is 97%). After distilling off the solvent, the residue is subjected to silica gel column chromatography, eluting with chloroform/methanol (1:0–1:0.01), to give diethyl 5-ethylpyridine-2,3-dicarboxylate (1.93 g., 84.6%). The product has a purity of 92.2% by liquid chromatographic analysis.

EXAMPLE 3

Diethyl 1-amino-1,2-ethylenedicarboxylate (5.0 g), α-ethylacrolein (2.82 g) and p-toluenesulfonic acid (0.1 g) are mixed. The mixture is heated at 100° C. for 18 hours. After adding thereto additional α-ethylacrolein (0.2 g), the mixture is heated at 100° C. for 3 hours to complete the reaction (the degree of reaction of aminodiester is 99.5%). The reaction mixture is treated in the same manner as described in Example 2 to give diethyl 5-ethylpyridine-2,3-dicarboxylate (4.3 g, 63.5%). The product has a purity of 87.7% by liquid chromatographic analysis.

EXAMPLES 4 to 18

Under the same molar ratio and reaction conditions as described in Example 2, there are reacted various enones (II) and aminodiesters (III) wherein $R^1$ to $R^5$ are varied as shown in Table 1, in Example 17 $R^1$ and $R^2$ in enones (II) being combined to form trimethylene, and in Example 18 $R^2$ and $R^3$ in enones (II) being combined to form pentamethylene. The results are shown in Table 1.

EXAMPLES 19 to 24

In the same manner as desribed in Example 2 except that the solvent shown in Table 2 is used instead of n-butanol and the reaction temperature is varies as shown in Table 2, the reaction is carried out. The results are shown in Table 2.

TABLE 1

| Ex. No. | $R^1$ | $R^2$ | $R^3$ | $R^4$ | $R^5$ | Degree of reaction (%) | Yield (%) | Purity (%) |
|---|---|---|---|---|---|---|---|---|
| 4 | H | H | $CH_3$ | $C_2H_5$ | $C_2H_5$ | 96.3 | 77.1 | 89.1 |
| 5 | $CH_3$ | H | $C_6H_5$ | $C_2H_5$ | $C_2H_5$ | 76.8 | 66.3 | 74.7 |

TABLE 1-continued

| Ex. No. | $R^1$ | $R^2$ | $R^3$ | $R^4$ | $R^5$ | Degree of reaction (%) | Yield (%) | Purity (%) |
|---|---|---|---|---|---|---|---|---|
| 6 | H | n-$C_4H_9$ | H | $C_2H_5$ | $C_2H_5$ | 95.2 | 85.7 | 91.6 |
| 7 | H | p-$ClC_6H_4$ | H | $C_2H_5$ | $C_2H_5$ | 95.5 | 79.5 | 90.7 |
| 8 | H | $CH_3OCH_2$ | H | $C_2H_5$ | $C_2H_5$ | 92.7 | 80.9 | 77.5 |
| 9 | H | $CF_3$ | H | $C_2H_5$ | $C_2H_5$ | 98.1 | 81.8 | 93.8 |
| 10 | H | $C_6H_5CH_2$ | H | $C_2H_5$ | $C_2H_5$ | 97.4 | 74.8 | 88.6 |
| 11 | H | p-$CH_3CONHC_6H_4$ | H | $C_2H_5$ | $C_2H_5$ | 93.1 | 85.9 | 84.4 |
| 12 | H | H | p-$ClC_6H_4$ | n-$C_4H_9$ | $C_2H_5$ | 88.0 | 79.8 | 93.9 |
| 13 | $C_6H_5$ | Cl | H | $CH_3$ | $C_2H_5$ | 70.6 | 66.7 | 90.8 |
| 14 | H | $C_2H_5O$ | H | $CH_3$ | $C_2H_5$ | 72.6 | 62.5 | 72.2 |
| 15 | H | $C_6H_5S$ | H | $C_2H_5$ | $C_2H_5$ | 75.4 | 60.8 | 69.7 |
| 16 | H | $CO_2CH_3$ | H | $C_2H_5$ | $C_2H_5$ | 98.8 | 68.5 | 78.5 |
| 17 | —$(CH_2)_3$— | | H | $C_2H_5$ | $C_2H_5$ | 89.2 | 69.7 | 80.8 |
| 18 | H | —$(CH_2)_5$— | | $C_2H_5$ | $C_2H_5$ | 93.5 | 88.5 | 90.4 |

TABLE 2

| Ex. No. | Solvent | Reaction temp. (°C.) | Reaction time (hr) | Degree of reaction (%) | Yield (%) | Purity (%) |
|---|---|---|---|---|---|---|
| 19 | Methanol | Reflux temp. | 40 | 78.2 | 57.8 | 88.3 |
| 20 | Isopropanol | " | 40 | 97.4 | 88.3 | 90.1 |
| 21 | sec-Butanol | " | 27 | 96.4 | 85.2 | 90.6 |
| 22 | Acetic acid | 50 | 10 | 100 | 68.4 | 98.2 |
| 23 | N,N-Dimethylformamide. | 120 | 13 | 98.8 | 63.7 | 90.8 |
| 24 | Dimethylsulfoxide | 100 | 15 | 97.4 | 58.4 | 92.4 |

What is claimed is:

1. A process for preparing pyridine-2,3-dicarboxylic acid compounds of the formula:

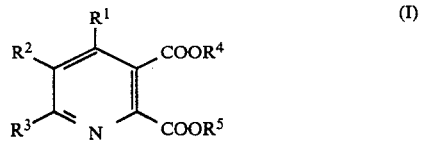
(I)

wherein $R^1$ and $R^3$ are the same or different and are each a hydrogen atom, a substituted or unsubstituted straight chain or branched chain alkyl having 1 to 4 carbon atoms, or a substituted or unsubstituted phenyl; $R^2$ is a hydrogen atom, a substituted or unsubstituted straight chain or branched chain alkyl having 1 to 4 carbon atoms, a substituted or unsubstituted phenyl, a straight chain or branched chain alkylthio having 1 to 4 carbon atoms, a straight chain or branched chain alkoxy having 1 to 4 carbon atoms, a substituted or unsubstituted phenylthio, a substituted or unsubstituted phenoxy, a halogen atom, a straight chain or branched chain alkoxycarbonyl having 1 to 4 carbon atoms in the alkoxy moiety, an aminocarbonyl which may optionally have a substituent, or cyano; or both of $R^1$ and $R^2$ or both $R^2$ and $R^3$ may combined together to form a divalent alkylene selected from trimethylene, tetramethylene and pentamethylene; and $R^4$ and $R^5$ are the same or different and are each a straight chain or branched chain alkyl having 1 to 4 carbon atoms, which comprises reacting an enone of the formula (II):

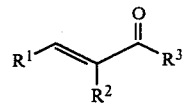

wherein $R^1$, $R^2$ and $R^3$ are as defined above with an aminodiester of the formula (III): $R^4OOCCH=C(NH_2)COOR^5$ wherein $R^4$ and $R^5$ are as defined above.

2. The process according to claim 1, wherein the reaction of the enone (II) and the aminodiester (III) is carried out without using any solvent.

3. The process according to claim 1, wherein the reaction of the enone (II) and the aminodiester (III) is carried out in a neutral organic solvent.

4. The process according to claim 1, wherein the reaction of the enone (II) and the aminodiester (III) is carried out in an organic carboxylic acid solvent.

5. The process according to claim 1, wherein the reaction of the enone (II) and the aminodiester (III) is carried out at a temperature of 50° to 150° C.

6. The process according to claim 1, wherein the reaction of the enone (II) and the aminodiester (III) is carried out in the presence of an acid catalyst.

* * * * *